(12) United States Patent
Willems et al.

(10) Patent No.: US 8,273,908 B2
(45) Date of Patent: Sep. 25, 2012

(54) PROCESS FOR THE PREPARATION OF ESTRONE AND/OR ESTRADIOL-DERIVATIVES

(75) Inventors: Lambertus Gerardus Maria Willems, Oss (NL); Henricus Johannes Franciscus Maas, Oss (NL); Martin Ostendorf, Oss (NL)

(73) Assignee: MSD Oss B.V., Oss (NL)

( * ) Notice: Subject to any disclaimer, the term of this patent is extended or adjusted under 35 U.S.C. 154(b) by 969 days.

(21) Appl. No.: 11/661,156

(22) PCT Filed: Aug. 22, 2005

(86) PCT No.: PCT/EP2005/054116
§ 371 (c)(1), (2), (4) Date: Feb. 22, 2007

(87) PCT Pub. No.: WO2006/021554
PCT Pub. Date: Mar. 2, 2006

(65) Prior Publication Data
US 2007/0299268 A1 Dec. 27, 2007

(30) Foreign Application Priority Data
Aug. 26, 2004 (EP) .................................... 04104089

(51) Int. Cl.
*C07J 1/00* (2006.01)
(52) U.S. Cl. ....................................... 552/625; 552/614
(58) Field of Classification Search .................. 552/614, 552/625
See application file for complete search history.

(56) References Cited

U.S. PATENT DOCUMENTS

| | | | |
|---|---|---|---|
| 3,186,907 | A | 6/1965 | Nomine et al. |
| 3,519,714 | A | 7/1970 | Hughes et al. |
| 4,400,524 | A | 8/1983 | Huber |
| 5,504,074 | A | 4/1996 | D'Amato et al. |
| 5,521,168 | A | 5/1996 | Clark |
| 5,661,143 | A | 8/1997 | D'Amato et al. |
| 5,892,069 | A | 4/1999 | D'Amato et al. |
| 6,051,726 | A | 4/2000 | Sachdeva et al. |
| 7,087,592 | B1 | 8/2006 | Agoston et al. |

FOREIGN PATENT DOCUMENTS

| | | |
|---|---|---|
| BE | 616293 | 10/1962 |
| DE | 3208432 | 9/1983 |
| EP | 0776904 | 3/2000 |
| GB | 2116165 | 9/1983 |
| WO | WO 02/42319 | 5/2002 |

OTHER PUBLICATIONS

International Search Report dated Nov. 21, 2005 and International Preliminary Report on Patentability dated Feb. 28, 2007 for PCT/EP2005/054116.
Ali et al.,"Synthesis and Receptor Binding Affinity of 7α- and 17α-Substituted 2- and 4-Chloroestradiol Derivatives," *J. Chem. Soc. Perkin Trans. 1* (1991) 2485-2491.
Axelrod et al., "Synthesis of 2-Hydroxyestradiol-17β," *Chem. & Ind.* (1959) 1454-1455.
Antonaccio, L.D., et. al., Preparation and Nuclear Magnetic Resonance Spectra of 11-Oxygenated Estrogen Catechols, J. Org. Chem., 36 (1971) 1832-1835.
Banerjee et al., "2-Methoxyestradiol inhibits estrogen-induced pituitary tumor angiogenesis and suppresses tumor growth in Fisher 344 rats," *Proc. Amer. Assoc. Cancer Res. 39*, (1998) 385.
Fishman, "Synthesis of 2-Methoxyestrogens," *J. Am. Chem. Soc.* 80(1958) 1213-1215.
Le Quesne et al., "Novel Synthesis of 2-Fluoroestradiol from 19-Nortestosterone: Biomimetic Oxidative Defluorination to 2-Hydroxyestradiol," *Steroids 53/6* (1989) 649-661.
Mihailovic et al., "A Novel Procedure for the Aromatization of Ring A in 19-Nortestosterone," *Tetrahedron 33* (1977) 235-237.
Greenspan, J. Am. Chem. Soc. 1946, 68(5), pp. 907.

*Primary Examiner* — Barbara P Badio
(74) *Attorney, Agent, or Firm* — Patricia L. Chisholm; Immac J. Thampoe

(57) ABSTRACT

Process for the preparation of a compound of general formula (II) wherein $R_1$ and $R_2$ independently are hydrogen or a hydroxy- or hydrocarbyl group; or wherein $R_1$ and $R_2$ together are a double bonded oxygen; $R_3$ is hydrogen; $R'_4$ is a nitrobenzophenone group; and $R_5$ and $R_6$ independently are hydrogen or a hydroxy- or hydrocarbyl group; from a compound of general formula (I) wherein, $R_1$, $R_2$ $R_3$, $R_5$ and $R_6$ are as defined above and $R_4$ is hydrogen; wherein the compound of formula (I) is reacted under alkaline conditions with 2-chloro-5-nitrobenzophenone in the presence of an alkanolic solvent and the compound of formula (II) is directly crystallized from this alkanolic solvent. Complex of an alkanol and a compound of general formula (II) obtainable from the above process and processes wherein the above process or complex are used.

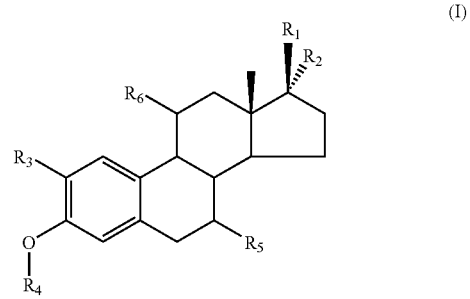

(I)

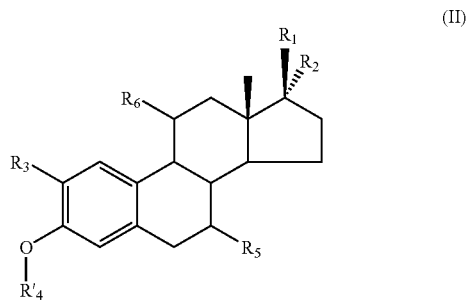

(II)

17 Claims, 2 Drawing Sheets

PROCESS FOR THE PREPARATION OF ESTRONE AND/OR ESTRADIOL-DERIVATIVES

TECHNICAL FIELD

Figure 1:
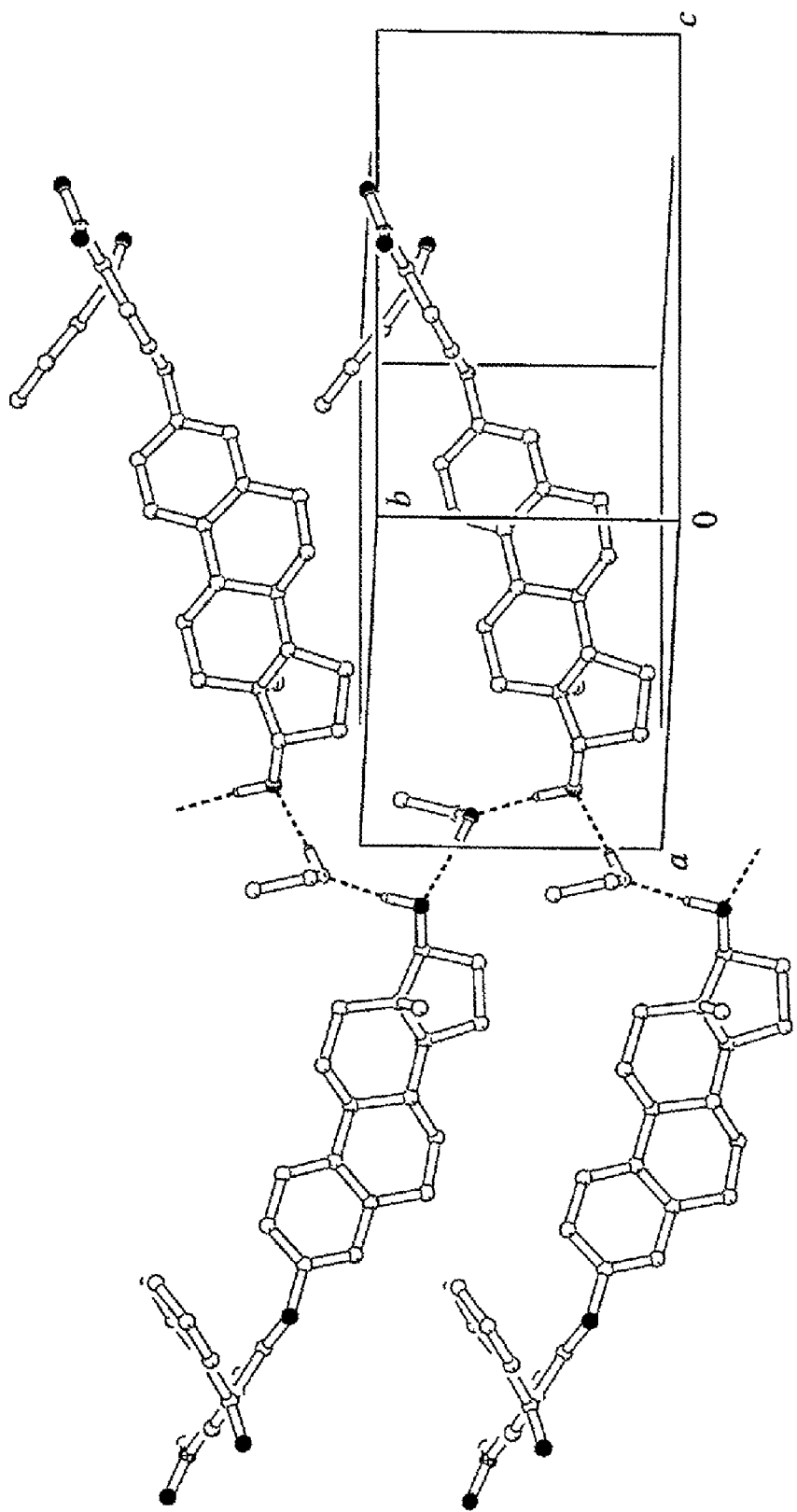

This invention relates to a process for the preparation of $\Delta^{1,3,5\ (10)}$-estratriene 3-(2-Benzoyl-4-nitro)-phenyl ether derivatives from 3-hydroxy-$\Delta^{1,3,5\ (10)}$-estratriene derivatives; complexes that can be generated in this process and processes in which such process or generated complex could be used.

BACKGROUND OF THE INVENTION

The therapeutic value of A-ring aromatic steroids such as estrone and estradiol are well known. In addition to the steroids itself, also derivatives of such steroids have been found to have therapeutic value. In this respect especially the 2-alkoxy-derivates of estrone and estradiol, such as 2-methoxy-3,17β-estradiol, need to be mentioned.

2-methoxy-3,17β-estradiol, also called 1,3,5(10)-estratrien-2,3,17β-triol-2-methyl-ether is an endogenous metabolite of estradiol. 2-methoxy-3,17β-estradiol has low estrogenic activity, but has been found to have important other biological effects, such as anti-cancer activity, as described herein below.

U.S. Pat. No. 5,504,074, U.S. Pat. No. 5,66,143 and U.S. Pat. No. 5,892,069 describe methods of treating mammalian diseases characterized by abnormal cell mitosis using 2-methoxy-3,17β-estradiol. In addition WO-A-02/42319 describes 2-methoxy-3,17β-estradiol for the treatment of disease states characterized by abnormal angiogenesis.

Undesirable cell mitosis is characteristic of many diseases, including, but not limited to, cancer, atherosclerosis, proliferation of solid tumours, vascular malfunctions, endometriosis, retinopathies, arthropathies, and abnormal wound healing. In addition, cell mitosis is important in a wide variety of biological functions, including but not limited to the normal development of the embryon, formation of the corpus luteum, cyclic proliferation of uterine endometrium, wound healing and inflammatory and immune responses.

U.S. Pat. No. 5,521,168 describes the use of 2-methoxy-3,17β-estradiol for lowering intraocular pressure. 2-methoxy-3,17β-estradiol also inhibits estrogen-induced pituitary tumour angiogenesis and suppresses tumour growth in Fisher 344 rats as reported by Banerjee, S. K. et al., Proc. Amer. Assoc. Cancer Res. 39, March 1998.

Processes for the preparation of 2-methoxy-3,17β-estradiol are known in the art. The article titled "Synthesis of 2-methoxyestrogens" by J. Fishman, published in the J. Am. Chem. Soc., 5 Mar. 1958, pages 1213-1216, describes the preparation of 2-methoxy-estradiol starting from estradiol. The first step of the described process comprises an etherification of estradiol with 2-chloro-5-nitrobenzophenone to its nitrobenzophenone ether. The described procedure for this step is, however, very cumbersome and results in a relatively low yield of about 45% m/m per turnover on starting compound estradiol. The etherification of estradiol with 2-chloro-5-nitrobenzophenone was carried out in an ethanolic potassium hydroxide solution. After refluxing for 48 hours the solution was concentrated to half the volume and poured into a sodium hydroxide solution. Hereafter the suspension was extracted 3 times with chloroform and after drying a yellow viscous oil was obtained. The oil was dissolved in a 1:1 petroleum ether-benzene mixture and chromatographed on alumina. Elution with benzene gave an oil which on trituration with ether crystallized as the estradiol nitrobenzophenone ether.

In subsequent steps the estradiol nitrobenzophenone ether is acetylated, followed by oxidation and methylation to give 2-methoxy-17β-acetoxy-$\Delta^{1,3,5\ (10)}$-estratriene 3-(2-Benzoyl-4-nitro)-phenyl ether. From this last compound 2-methoxy-3,17β-estradiol can be prepared by either hot alkaline hydrolysis or by piperidine cleavage followed by hydrolysis with ethanolic potassium hydroxide.

A disadvantage of this process is the fact that the first step is very time-consuming and can take up to 60 hours. Such a time-consuming process step is especially unattractive when the process is to be applied at an industrial scale. Moreover, the first step results in a relatively poor yield of only 45% m/m.

Advantageously, a process has now been found which allows the first step to be carried out at an industrial scale within an economically attractive timeframe. With the process according to the invention the first step can be carried out within less than about 20 hours and, if desirable, even within less than 10 hours. In addition higher yields can be obtained.

SUMMARY OF THE INVENTION

Accordingly this invention provides a process for the preparation of a compound of general formula II

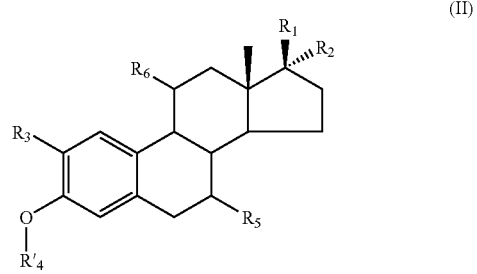

wherein $R_1$ and $R_2$ independently are hydrogen or a hydroxy- or hydrocarbyl group; or wherein $R_1$ and $R_2$ together are a double bonded oxygen; $R_3$ is hydrogen; $R'_4$ is a nitrobenzophenone group; and $R_5$ and $R_6$ independently are hydrogen or a hydroxy- or hydrocarbyl group;
from a compound of general formula I

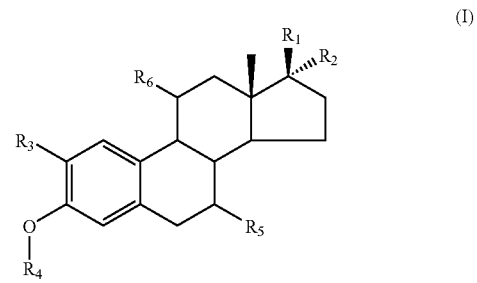

wherein, $R_1$, $R_2$ $R_3$, $R_5$ and $R_6$ are as defined above and $R_4$ is hydrogen,
wherein the compound of general formula I is reacted under alkaline conditions with 2-chloro-5-nitrobenzophenone in the presence of an alkanolic solvent and the compound of formula II is directly crystallized from this alkanolic solvent.

The process according to the invention results in an advantageous decrease of process time which makes the process economically attractive for application at an industrial scale.

In addition the process according to the invention generates a complex of an alkanol and the compound of general formula II, which is considered to be novel. Hence the present invention also provides a complex of an alkanol and a compound of general formula II

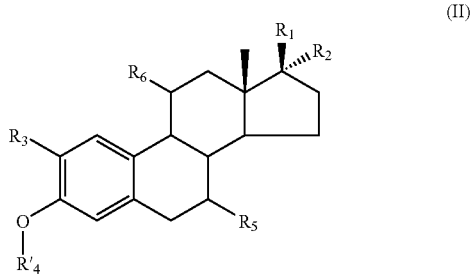

(II)

wherein $R_1$ and $R_2$ independently are hydrogen or a hydroxy- or hydrocarbyl group; or wherein $R_1$ and $R_2$ together are a double bonded oxygen; $R_3$ is hydrogen; $R'_4$ is a nitrobenzophenone group; and $R_5$ and $R_6$ independently are hydrogen or a hydroxy- or hydrocarbyl group;
obtainable from a process comprising crystallization of the compound of general formula II from a solution in such an alkanol.

FIGURES

Figure 2:
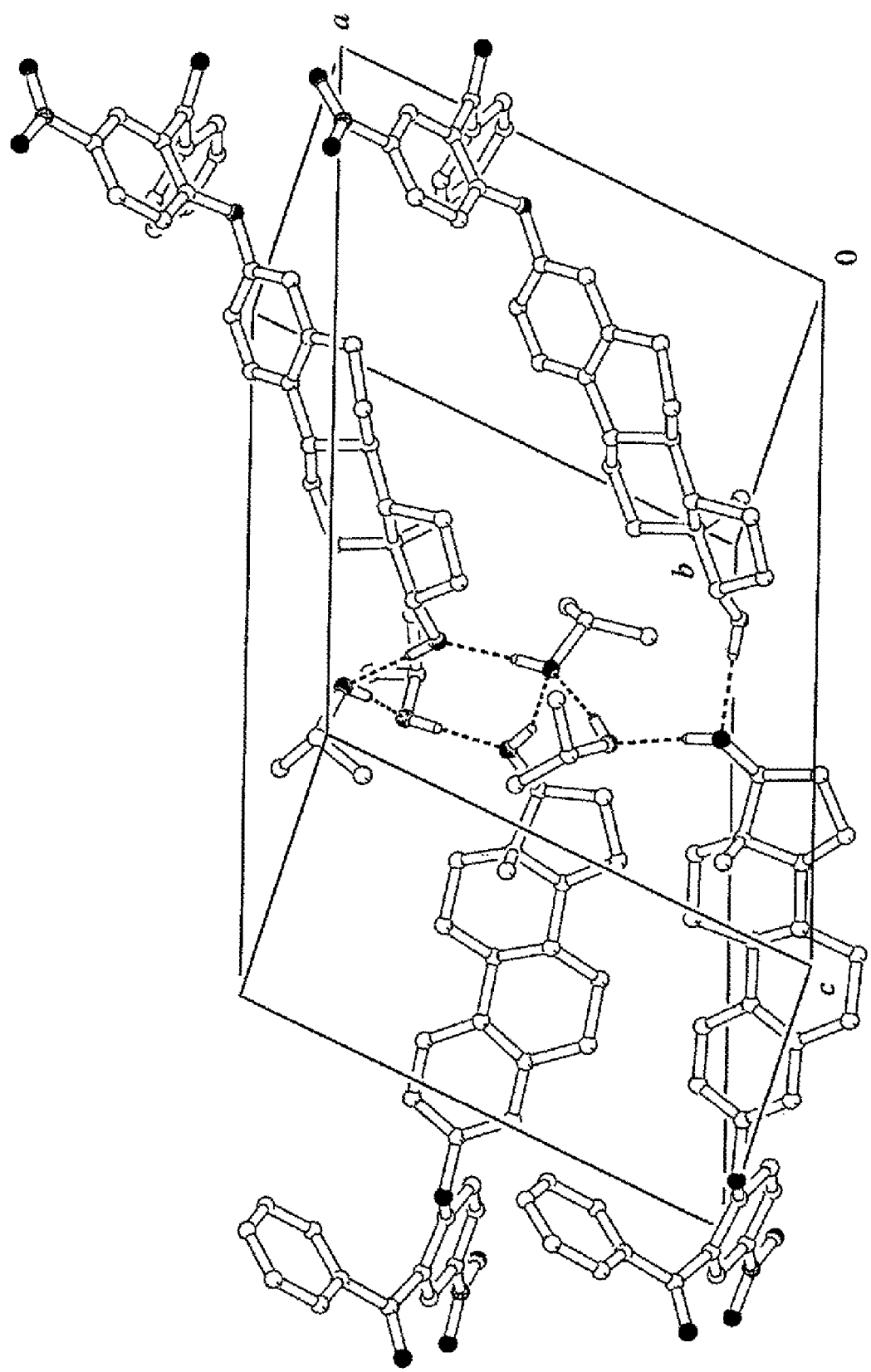

The following figures have been enclosed to illustrate the present invention:
FIG. 1:
Crystal structure of 17β-hydroxy-$\Delta^{1,3,5\ (10)}$-estratriene 3-(2-benzoyl-4-nitro)-phenyl ether-isopropanol complex.
FIG. 2:
Crystal structure of 17β-hydroxy-$\Delta^{1,3,5\ (10)}$-estratriene 3-(2-benzoyl-4-nitro)-phenyl ether-ethanol complex.

DETAILED DESCRIPTION OF THE INVENTION

In the process according to the invention $R_1$ and $R_2$ can independently be hydrogen or a hydroxy- or hydrocarbyl group. By a hydrocarbyl group is understood any group comprising one or more hydrogen atoms as well as one or more carbon atoms. Examples of such a group include substituted or non-substituted alkyl, aryl, alkylaryl and arylalkyl groups. Preferably the hydrocarbyl-group comprises from 1 to 20 carbon atoms, more preferably from 1 to 10 carbon atoms and most preferably from 1 to 6 carbon atoms. Such a group can further comprise one or more heteroatoms such as for example S, O, F, Br, Cl, I, P or N. Specific examples of hydrocarbyl-groups include methyl, ethyl, propyl, methyl isopropyl, butyl, isobutyl, tert.-butyl, pentyl, isopentyl, hexyl, phenyl, benzyl and tolyl. In a further embodiment $R_1$ is a hydroxy group whilst $R_2$ is hydrogen.

$R_5$ and $R_6$ independently can be hydrogen or a hydroxy- or hydrocarbyl group. Examples of hydrocarbyl groups are such as described above for $R_1$ and $R_2$. In a further embodiment $R_5$ and $R_6$ are both hydrogen.

In a specific embodiment the invention provides a process wherein in the compound of general formula I and in the compound of general formula II, $R_1$ is a hydroxy group and $R_2$ is hydrogen; or wherein $R_1$ and $R_2$ together are a double bonded oxygen; and wherein $R_5$ and $R_6$ are hydrogen groups.

In a further embodiment the compound of formula I is 3,17β-estradiol; the compound of formula II is 17β-hydroxy-$\Delta^{1,3,5\ (10)}$-estratriene 3-(2-benzoyl-4-nitro)-phenyl ether; and the invention provides a process for the preparation of 17β-hydroxy-$\Delta^{1,3,5\ (10)}$-estratriene 3-(2-benzoyl-4-nitro)-phenyl ether from 3,17β-estradiol, wherein 3,17β-estradiol is reacted under alkaline conditions with 2-chloro-5-nitrobenzophenone in the presence of an alkanolic solvent to yield 17β-hydroxy-$\Delta^{1,3,5\ (10)}$-estratriene 3-(2-Benzoyl-4-nitro)-phenyl ether, which is directly crystallized from such alkanolic solvent.

The alkanol that is used as an alkanolic solvent in the process of the invention can be any alkanol. The alkanol can be a mono-alkanol or a polyalkanol such as for example alkadiol or alkatriol. In one embodiment the alkanol is a mono-alkanol. In a further embodiment the alkanol is a C1-C6-monoalkanol comprising from 1 to 6 C-atoms. Suitable examples of alkanols include methanol, ethanol, n-propanol, isopropanol, n-butanol, isobutanol, tert-butanol, n-pentanol, iso-pentanol, tert-pentanol; and hexanol. In an even further embodiment the alkanol is a C2-C6 mono-alkanol comprising from 2 to 6 C-atoms and in a still further embodiment it is a C2-C4 mono-alkanol preferably chosen from the group consisting of ethanol, propanol, isopropanol, butanol, isobutanol and tert.-butanol. In an still further embodiment the alkanol is ethanol or an propanol. Especially isopropanol has been found very suitable in the process of the invention.

In another embodiment an alkanol with a boiling point in the range from 60 to 100° C., or more preferably in the range from 75° C. to 100° C., is used in the process of the invention. Such an alkanol enables the advantageous use of a relatively high reaction temperature, such as for example in the range from 60° to 100° C. or more preferably in the range from 75° to 100° C.

In a further embodiment the weight ratio of the amount of alkanolic solvent to the amount of compound of general formula I lies in the range from 1:5 to 1:50 and more preferably in the range from 1:10 to 1:20.

In a still further embodiment the molar ratio of the amount of compound of general formula I to the amount of 2-chloro-5-nitrobenzophenone lies in the range from 1:2 to 2:1 and more preferably from 1:0.9 to 1:1.5. In an even further embodiment this molar ratio lies in the range from 1:1 to 1:1.4 and still further in the range from 1:1.1 to 1:1.3.

By a reaction under alkaline conditions is understood that the compound of general formula I is reacted with 2-chloro-5-nitrobenzophenone in the presence of a base. Suitable bases include for example sodium hydroxide, potassium hydroxide, lithium hydroxide, sodium hydride, potassium hydride and lithium di-isopropyl-diamide. In one embodiment the compound of formula I is dissolved in a basic alkanolic solution, whereafter the 2-chloro-5-nitrobenzophenone is added to the solution and reaction takes place. The reaction can be carried out at atmospheric pressure. In a preferred embodiment the reaction is carried out at reflux temperature of the alkanol. In an even further embodiment this temperature lies in the range from 60 to 100° C. After the reaction the reaction mixture can be filtered to remove solid byproducts.

Subsequently the compound of general formula II can be directly crystallized from the alkanolic solution.

In a still further embodiment the invention provides a process as described hereinabove, wherein the compound of formula II is crystallized directly from the alkanolic solvent as an alkanolic complex, i.e. as a complex of the alkanol and the compound of formula II. The alkanolic complex is preferably at least partly present as crystalline particles. Crystalline particles are precipitates of solid matter in which the individual molecules are ordered in a regular pattern. The particles generated are composed of crystals or fragments of crystals. In the latter case, the several fragments can be separated by amorphous regions.

It was found that such complexes are also novel and hence this invention also provides such complexes as stated above.

In a preferred embodiment the complex is a complex of an alkanol and a compound of general formula II, wherein $R_1$ is an hydroxy group and $R_2$ is hydrogen; or wherein $R_1$ and $R_2$ together are a double bonded oxygen; and wherein $R_5$ and $R_6$ are hydrogen groups. In a further embodiment the alkanol in such a complex is a C2-C6 mono-alkanol, as described above. In a still further embodiment the alkanol is selected from the group of ethanol, n- and iso-propanol and butanol.

In a further preferred embodiment a novel complex of 17β-hydroxy-$\Delta^{1,3,5\ (10)}$-estratriene 3-(2-Benzoyl-4-nitro)-phenyl ether and such an alkanol is prepared. Examples of such a complex wherein the alkanol is ethanol and isopropanol, have been illustrated in FIGS. 1 and 2.

The novel process and/or complex according to the invention can advantageously be used in subsequent processing steps, for example in subsequent processing steps to prepare 2-alkoxy-derivates of estrone and estradiol, such as 2-methoxy estrone or 2-methoxy-estradiol.

Hence, the present invention further provides a process for the preparation of a compound with general formula III

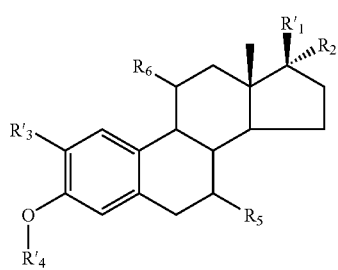

(III)

wherein $R'_1$ is an ester-group of the formula —O—C(O)—$R_7$, wherein $R_7$ represents hydrogen or an alkyl group having from 1 to 3 C atoms; $R_2$ is hydrogen or an hydrocarbyl group; $R'_3$ is a hydroxy group; $R'_4$ is a nitrobenzophenone group; and $R_5$ and $R_6$ independently are hydrogen or a hydroxy- or hydrocarbyl group; in one or more steps from a compound of general formula II

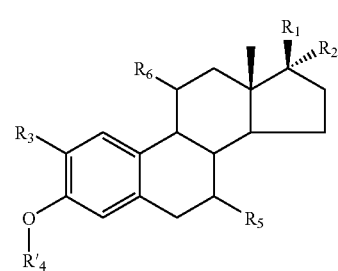

(II)

wherein $R_1$ is an hydroxy group; $R_2$ is hydrogen or an hydrocarbyl group; $R_3$ is hydrogen; $R'_4$ is a nitrobenzophenone group; and $R_5$ and $R_6$ independently are hydrogen or a hydroxy- or hydrocarbyl group; and wherein the compound of general formula II is supplied as an alkanolic complex.

In a further embodiment $R_2$, $R_5$ and $R_6$ in the compound of general formula II and III are all hydrogen.

In a further embodiment the present invention provides such a process, wherein the alkanol in the alkanolic complex is a C2-C6 mono-alkanol. In a still further embodiment the alkanol is a C2-C4 mono-alkanol such as ethanol, n- and iso-propanol and butanol.

In an even further embodiment such a process is provided, wherein the starting compound is supplied as a complex of 17β-hydroxy-$\Delta^{1,3,5\ (10)}$-estratriene 3-(2-Benzoyl-4-nitro)-phenyl ether and isopropanol or ethanol.

Such a process for the preparation of a compound with general formula III, and especially for the preparation of 2-hydroxy-17β-acetoxy-$\Delta^{1,3,5\ (10)}$-estratriene 3-(2-Benzoyl-4-nitro)-phenyl ether, can be carried out in any manner known in the art, including for example the acetylation and/or oxidation as described by J. Fishman in his article titled "Synthesis of 2-methoxyestrogens". The process can for example include an acetylation of 17β-hydroxy-$\Delta^{1,3,5\ (10)}$-estratriene 3-(2-benzoyl-4-nitro)-phenyl ether of 3,17β-estradiol using pyridine as a solvent to give the non-crystalline 17β-acetoxy-$\Delta^{1,3,5\ (10)}$-estratriene 3-(2-Benzoyl-4-nitro)-phenyl ether. The latter can for example subsequently be oxidized with hydrogen peroxide resulting in a 2-hydroxy-17β-acetoxy-$\Delta^{1,3,5\ (10)}$-estratriene 3-(2-Benzoyl-4-nitro)-phenyl ether.

In a further embodiment the steps of acetylation and oxidation in such a process are advantageously combined in one pot. Hence, the present invention also provides a one-pot process for the preparation of a compound with general formula III

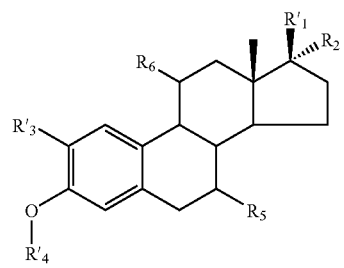

(III)

wherein $R'_1$ is an ester-group of the formula —O—C(O)—$R_7$, wherein $R_7$ represents hydrogen or an alkyl group having from 1 to 3 C atoms; $R_2$ is hydrogen or an hydrocarbyl group; $R'_3$ is a hydroxy group; $R'_4$ is a nitrobenzophenone group; and $R_5$ and $R_6$ independently are a hydrogen or a hydroxy- or hydrocarbyl group;

from a compound of general formula II

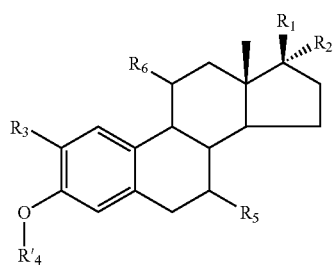

(II)

wherein $R_1$ is an hydroxy group; $R_2$ is hydrogen or an hydrocarbyl group; $R_3$ is hydrogen; $R'_4$ is a nitrobenzophenone group; and $R_5$ and $R_6$ independently are hydrogen or a hydroxy- or hydrocarbyl group;

comprising a) esterification of the $R_1$ hydroxy group in the compound of general formula II by reacting such compound with an excess of an acid anhydride of the formula $R_7$—C(O)—O—C(O)—$R_7$, wherein $R_7$ represents hydrogen or an alkyl group having from 1 to 3 C atoms, in the presence of a first acid, which first acid is soluble in the acid anhydride; yielding a reaction mixture containing the first acid, the 17β-ester-derivative of the compound of general formula II, an acid of the formula HO—C(O)—$R_7$, wherein $R_7$ represents hydrogen or an alkyl group having from 1 to 3 C atoms, and residual acid anhydride;

b) addition of a sufficient amount of water to convert the residual acid anhydride to an acid of the formula HO—C(O)—$R_7$, wherein $R_7$ represents hydrogen or an alkyl group having from 1 to 3 C atoms; yielding a reaction mixture containing the first acid, the 17β-ester-derivative of the compound of general formula II, the acid of formula HO—C(O)—$R_7$, and optionally any residual water;

c) addition of a second acid, yielding a reaction mixture containing a complex of such acid and the 17β-ester-derivative of the compound of general formula II;

d) oxidation of the $R_3$ hydrogen group in the 17β-ester-derivative by addition of an, optionally prepared in-situ, organic peroxoic acid, within a time period of 30 minutes; yielding a mixture comprising the compound of general formula III, an acid of the formula HO—C(O)—$R_7$, wherein $R_7$ represents hydrogen or an alkyl group having from 1 to 3 C atoms, and optionally any residual water and/or organic peroxoic acid.

The above combination of acetylation and oxidation in one pot does not only have economic advantages. The process also has an advantage in that it directly generates a crystalline, solid product and makes it possible to avoid working with a viscous oil or pyridine as described in the article of J. Fishman cited above.

In a further embodiment $R_7$ represents hydrogen, methyl, ethyl, propyl, or isopropyl group. In an even further embodiment $R_7$ represents an alkyl group having from 1 to 3 carbon atoms. In a still further embodiment $R_7$ represents an methyl group, such that the acid anhydride in step a) is acetic acid anhydride; the 17β-ester-derivative is a 17β-acetoxy-derivative; and the acid of the formula HO—C(O)—$R_7$ is acetic acid.

In a further embodiment the excess of acid anhydride can simultaneously be used as solvent. The acid anhydride in step a) is at least present in a supra-equimolar amount in respect of the amount of compound of general formula II.

Although higher amounts can be used, for practical purposes it can be desirable to choose an amount of acid anhydride up to about 100 molar equivalents in respect of the amount of compound of general formula II. In a further embodiment the molar ratio of amount of acid anhydride to compound of general formula II lies in the range from 5:1 to 50:1.

In a further embodiment the first acid mentioned in step a) is an acid having a pKa value of less than 4, preferably less than 3, and more preferably less than 2, measured in aqueous solution at 25° C. Examples of acids that can be used as a first acid include phosphoric acid, sulphuric acid, hydrogen halides, sulphonic acids and halogenated carboxylic acids such as trifluoroacetic acid. Sulphonic acids are in particular preferred, for example methanesulphonic acid, trifluoromethanesulphonic acid, tert-butanesulphonic acid, p-toluenesulphonic acid and 2,4,6-trimethylbenzenesulphonic acid.

After the reaction in step a) a certain amount of acid of the formula HO—C(O)—$R_7$ is already present. In a further embodiment a sufficient amount of water is added in step b) to react with any remaining acid anhydride of step a) such that no or essentially no acid anhydride remains. The amount of water added is preferably such that after addition nearly all water has reacted with the acid anhydride and not more than 1.0% v/v and more preferably between 0.1 and 1.0% v/v of water remains.

In a further embodiment the second acid in step c) is an acid having a pKa in aqueous solution at 25° C. of less than 2 and in a still further embodiment of less than 1. Examples of acids that can be used include nitric acid, sulphuric acid and perchloric acid. In a special embodiment the second acid is sulphuric acid.

In a further embodiment the organic peroxoic acid in step d) is an organic peroxoic acid having from 1 to 6 carbon atoms, such as for example methane peroxoic acid, ethane peroxoic acid, propane peroxoic acid, butane peroxoic acid, pentane peroxoic acid and hexane peroxoic acid. In a preferred embodiment the organic peroxoic acid is ethane peroxoic acid (also sometimes called acetic peroxoic acid).

The organic peroxoic acid can be added as such or can be prepared in situ in the reaction mixture by reaction of a hydrogen peroxide with a suitable second acid. For example, the organic peroxoic acid can be prepared in situ by adding hydrogen peroxide to the reaction mixture which is already comprising acid of the formula HO—C(O)—$R_7$ yielding an organic peroxoic acid of the formula $R_7$—$CO_3H$, wherein $R_7$ represents hydrogen or an alkyl group having from 1 to 3 C atoms. For example, hydrogen peroxide can be added to a mixture comprising acetic acid, thereby preparing in situ acetic peroxoic acid, which peroxoic acid can subsequently oxidise the $R_3$ hydrogen group in the 17β-ester-derivative.

In a further embodiment the organic peroxoic acid is added in step d) in a molar ratio to the starting compound of general formula II in the range from 1:1 to 1:5. In a still further embodiment it is added in such a molar ratio in the range from 1:1 to 1:2.

In a further embodiment the organic peroxoic acid is added within a time period of 25 minutes and in a still further embodiment within a period of 20 minutes. In a special embodiment the organic peroxoic acid is added within a period of 15 minutes. If the organic peroxoic acid is prepared in situ, such addition can be achieved by for example adding hydrogen peroxide within this period.

The reaction can be carried out in a wide range of temperatures. For example a temperature in the range from 0° C. to 100° C. can be applied independently in step a) and/or steps b), c) and/or d). Preferably a temperature in the range from 20° C. to 80° C. is applied independently in a) and/or steps b), c) and/or d). The addition of the organic peroxoic acid in step d) is preferably carried out at a temperature in the range between 25° C. to 45° C. and more preferably at a temperature in the range between 30° C. and 40° C.

In addition a wide range of pressures can be applied. Preferably, however, the reaction in step a) and/or steps b), c) and/or d) is carried out at atmospheric pressure.

In a further embodiment the ratio at the end of step b) of amount in liters of HO—C(O)—$R_6$ acid in step a) together with the water in step b) to amount in kg of 17β-ester-derivative in the reaction mixture lies in the range from 4:1 to 6:1.

In a still further embodiment steps a), b), c) and d) of the above process are further followed by an optional step e) comprising the neutralization of any remaining organic peroxoic acid and/or hydrogen peroxide; and an optional step f) comprising the washing and purification of the product.

In a further embodiment the present invention provides such a process wherein 2-hydroxy-17β-acetoxy-$\Delta^{1,3,5\,(10)}$-estratriene 3-(2-Benzoyl-4-nitro)-phenyl ether is prepared from 17β-hydroxy-$\Delta^{1,3,5\,(10)}$-estratriene 3-(2-Benzoyl-4-nitro)-phenyl ether.

In a further embodiment such a process comprises the steps of:

Reacting 17β-hydroxy-$\Delta^{1,3,5\,(10)}$-estratriene 3-(2-Benzoyl-4-nitro)-phenyl ether with acetic acid anhydride in the presence of p-toluene-sulfonic acid. This step can for example be carried out by using an amount of 24 molar equivalent acetic acid in respect of the ether, at for example 70° C., whilst using e.g. 1 mol % p-toluene-sulfonic acid.

Addition of water. This step can for example be carried out by using an amount of 22 molar equivalents water in respect of the ether, and at for example 60° C.

Addition of sulphuric acid. This step can for example be carried out by using an amount of 15 molar equivalents sulphuric acid in respect of the ether, and at for example 33° C.

And addition of ethane peroxoic acid, within a time period of 30 minutes, to generate 2-hydroxy-17β-acetoxy-$\Delta^{1,3,5\,(10)}$-estratriene 3-(2-Benzoyl-4-nitro)-phenyl ether. This step can for example be carried out by using an amount of 2 molar equivalents ethane peroxoic acid in respect of the ether, and at for example 33° C.

Hereafter aqueous sodium sulphate can be added, the product can be crystallized and washed neutral with sodiumacetate. A toluene/charcoal treatment might be given and the final product might be crystallized from methanol.

The compound with general formula III can subsequently be alkylated to a compound with general formula IV:

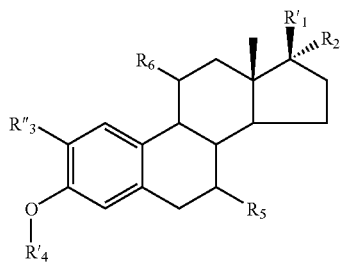

(IV)

wherein $R'_1$ is an ester-group of the formula —O—C(O)—$R_7$, wherein $R_7$ represents hydrogen or an alkyl group having from 1 to 3 C atoms; $R_2$ is hydrogen or an hydrocarbyl group; $R''_3$ is an alkoxy group; $R'_4$ is a nitrobenzophenone group; and $R_5$ and $R_6$ independently are hydrogen or a hydroxy- or hydrocarbyl group.

In a further embodiment $R_2$, $R_5$ and $R_6$ in the compound of general formula IV are all hydrogen. Moreover, in an even further embodiment $R_7$ represents an alkyl group having from 1 to 3 carbon atoms.

The 2-alkoxy group $R''_3$ can be any alkoxy group known in the art. In one embodiment the alkoxy group is a C1-C6 alkoxy group and in a further embodiment the alkoxy group is a C1-C4 alkoxy group. Examples of suitable alkoxy groups include methoxy, ethoxy, propoxy, butoxy and pentoxy. In a special embodiment the alkoxy group $R''_3$ is a methoxy group.

In a further embodiment such a process comprises the alkylation of 2-hydroxy-17β-acetoxy-$\Delta^{1,3,5\,(10)}$-estratriene-3-(2-Benzoyl-4-nitro)-phenyl ether into 2-alkoxy-17β-acetoxy-$\Delta^{1,3,5\,(10)}$-estratriene 3-(2-Benzoyl-4-nitro)-phenyl ether and in a special embodiment the methylation into 2-methoxy-17β-acetoxy-$\Delta^{1,3,5\,(10)}$-estratriene 3-(2-Benzoyl-4-nitro)-phenyl ether.

Such a process for the preparation of a compound with general formula IV, and especially the alkylation of 2-hydroxy-17β-acetoxy-$\Delta^{1,3,5\,(10)}$-estratriene-3-(2-Benzoyl-4-nitro)-phenyl ether to 2-alkoxy-17β-acetoxy-$\Delta^{1,3,5\,(10)}$-estratriene 3-(2-Benzoyl-4-nitro)-phenyl ether, can be carried out in any manner known in the art, including for example the methylation with help of diazomethane as described by J. Fishman in his article titled "Synthesis of 2-methoxyestrogens".

In a preferred embodiment, however, the alkylation is carried out using so-called Mitsunobu reagentia, e.g. by combining the compound with general formula III with a dialkylazodicarboxylate, triphenylphosphine and a suitable alkanol in a suitable solvent. In a special embodiment the alkanol is methanol and the alkylation is a methylation. Furthermore a wide range of solvents can be used. In a special embodiment, however, the solvent used is toluene. The reaction can be carried out at various temperatures and pressures. In a specific embodiment however the reaction can be carried out at atmospheric pressure whilst using a temperature in the range from 20° C. to 60° C.

The compound with general formula IV can subsequently be hydrolysed into a general formula V

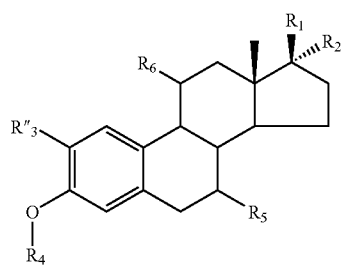

(V)

wherein $R_1$ is an hydroxy group; $R_2$ is hydrogen or an hydrocarbyl group; $R''_3$ is an alkoxy group; $R_4$ is hydrogen; and $R_5$ and $R_6$ independently are hydrogen or a hydroxy- or hydrocarbyl group.

In a further embodiment $R_2$, $R_5$ and $R_6$ in the compound of general formula V are all hydrogen.

The hydrolysis can be carried out in any manner known in the art, for example by hot alkaline hydrolysis or by piperidine cleavage followed by hydrolysis with ethanolic potassium hydroxide. Such a hot alkaline hydrolysis can for example be carried out with $K_2CO_3$ in an alkanol such as methanol at reflux temperature.

In a further embodiment such a process comprises the hydrolysis of an 2-alkoxy-17β-acetoxy-$\Delta^{1,3,5\,(10)}$-estratriene 3-(2-Benzoyl-4-nitro)-phenyl ether, such as 2-methoxy-17β-acetoxy-$\Delta^{1,3,5\,(10)}$-estratriene 3-(2-Benzoyl-4-nitro)-phenyl ether, to an 2-alkoxy-3,17β-estradiol such as 2-methoxy-3,17β-estradiol.

The invention therefore provides an advantageous process for the preparation of an 2-alkoxy-$\Delta^{1,3,5\,(10)}$-estratriene-derivative with general formula V

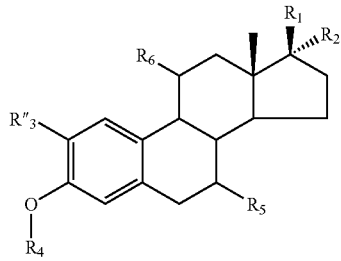

wherein $R_1$ is an hydroxy group; $R_2$ is hydrogen or an hydrocarbyl group; $R''_3$ is an alkoxy group; $R_4$ is hydrogen; and $R_5$ and $R_6$ independently are hydrogen or a hydroxy- or hydrocarbyl group;
from a compound of general formula I

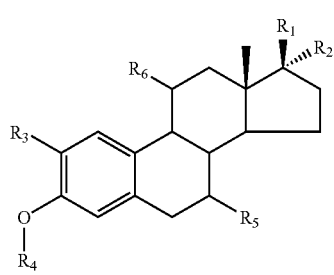

wherein, $R_1$, $R_2$, $R_4$, $R_5$ and $R_6$ are as defined above and $R_3$ is hydrogen;
by using any of the above processes and/or the above mentioned complex.

The process and/or the complex according to the invention can advantageously be used in a process for the preparation of an 2-alkoxy-3,17β-estradiol, such as 2-methoxy-3,17β-estradiol, and the invention hence also provides a process for the preparation of such an 2-alkoxy-3,17β-estradiol from 3,17β-estradiol wherein the above mentioned process and/or the above mentioned complex is used.

In a further embodiment the present invention provides a process for the preparation of a 2-alkoxy-derivates of 3,17β-estradiol comprising the steps of
a) reacting 3,17β-estradiol to the 17β-hydroxy-$\Delta^{1,3,5\,(10)}$-estratriene 3-(2-benzoyl-4-nitro)-phenyl ether thereof according to the process as described above;
b) reacting the 17β-hydroxy-$\Delta^{1,3,5\,(10)}$-estratriene 3-(2-benzoyl-4-nitro)-phenyl ether of 3,17β-estradiol in one or more steps to a 2-alkoxy-derivates of 3,17β-estradiol.

The preparation of the 2-methoxy-derivative of 3,17β-estradiol is especially advantageous, because of the wide applicability of this compound and the desire to prepare this compound on an industrial scale.

The invention is further illustrated by the following non-limiting examples.

Comparative Example A

A solution containing KOH (15.3 g, 273 mmol), 3,17β-estradiol (75 g, 275 mmol) and 2-chloro-5-nitrobenzophenone (69.4 g, 262 mmol) in isopropanol (1.6 L, corresponding to about 1.3 kg) was heated at reflux for 20 h. After cooling to room temperature, the reaction mixture was filtrated and concentrated in vacuo to a volume of 480 mL and poured out into an aqueous NaOH solution (1.0 M, 4.0 L). The product was filtered off and taken up in dichloromethane (750 mL). The organic layer was washed with brine (10% aqueous NaCl solution, 2×75 mL), filtered, and the solvent was replaced by diethyl ether. The product was filtered off and dried in vacuo at 50° C. The yield consisted of brown crystals (93.5 g, 188 mmol) in 68% mol/mol based on starting amount of 3,17β-estradiol.

Example 1

A solution containing KOH (20.3 kg, 362 mol), 3,17β-estradiol (75 kg, 275 mol) and 2-chloro-5-nitrobenzophenone (88.5 kg, 338 mol) in isopropanol (1350 L, corresponding to about 1060 kg) was heated at reflux for 3 h. After cooling to room temperature, the reaction mixture was filtrated and concentrated in vacuo to a volume of 870 L. The product was filtered off and dried in vacuo at 50° C. The yield consisted of yellow crystals (115.8 kg, 233 mol) in 85% mol/mol based on starting amount of 3,17β-estradiol.

The crystal structure of the generated 17β-hydroxy-$\Delta^{1,3,5\,(10)}$-estratriene 3-(2-benzoyl-4-nitro)-phenyl ether-isopropanol complex crystals is visualized in FIG. 1.

Example 2

Reaction in Methanol

A solution containing KOH (8.0 g, 143 mmol), 3,17β-estradiol (30.0 g, 110 mmol) and 2-chloro-5-nitrobenzophenone (34.5 g, 132 mmol) in methanol (550 mL, corresponding to about 435 g) was heated at reflux for 22 h. The reaction mixture was filtrated and concentrated in vacuo to a volume of 350 mL. Upon cooling to −10° C., the product crystallized. The product was filtered off and dried in vacuo at 50° C. The yield consisted of yellow crystals (38.1 g, 76.6 mmol) in 70% mol/mol based on starting amount of 3,17β-estradiol. Methanol content was 0.2% w/w (measured by gas chromatography).

Example 3

Reaction in Ethanol

A solution containing KOH (2.7 g, 48 mmol), 3,17β-estradiol (10.0 g, 37.7 mmol) and 2-chloro-5-nitrobenzophenone (11.5 g, 43.9 mmol) in ethanol (280 mL) was heated at reflux for 3 h. The reaction mixture was filtrated and concentrated in vacuo to a volume of 160 mL. Upon cooling to 6° C., the product crystallized. The product was filtered off and dried in vacuo at 50° C. The yield consisted of yellow crystals (14.0 g, 28.1 mmol) in 77% mol/mol based on starting amount of 3,17β-estradiol. Ethanol content was 3.5% w/w measured by gas chromatography).

The crystal structure of the generated 17β-hydroxy-$\Delta^{1,3,5\,(10)}$-estratriene 3-(2-benzoyl-4-nitro)-phenyl ether-ethanol complex crystals is visualized in FIG. 2.

The invention claimed is:

1. A process for the preparation of a compound of formula II

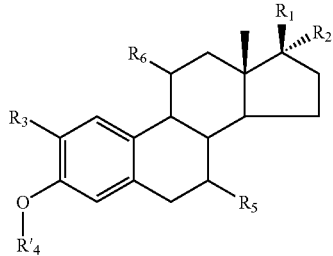

(II)

wherein $R_1$ and $R_2$ independently are hydrogen or a hydroxy- or hydrocarbyl group; or wherein $R_1$ and $R_2$ together are a double bonded oxygen; $R_3$ is hydrogen; $R'_4$ is a nitrobenzophenone group; and $R_5$ and $R_6$ independently are hydrogen or a hydroxy- or hydrocarbyl group;
from a compound of formula I

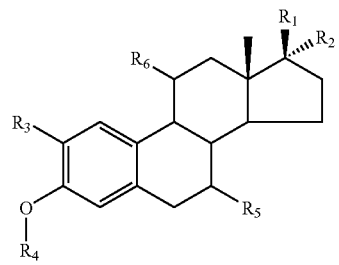

(I)

wherein, $R_1$, $R_2$, $R_3$, $R_5$ and $R_6$ are as defined above and $R_4$ is hydrogen;
wherein the compound of formula I is reacted under alkaline conditions with 2-chloro-5-nitrobenzophenone in the presence of an alkanolic solvent and the compound of formula II is directly crystallized from this alkanolic solvent.

2. The process according to claim 1, wherein in the compound of formula I and in the compound of formula II $R_1$ is an hydroxy group and $R_2$ is hydrogen; or wherein $R_1$ and $R_2$ together are a double bonded oxygen; and wherein $R_5$ and $R_6$ are hydrogen groups.

3. A process according to claim 1, wherein the alkanol is a C2-C6 mono-alkanol.

4. The process according to claim 1, wherein the compound of formula II is crystallized from the alkanolic solvent as an alkanolic complex.

5. A process according to claim 2, wherein the alkanol is a C2-6 mono-alkanol.

6. The process according to claim 2, wherein the compound of formula II is crystallized from the alkanolic solvent as an alkanolic complex.

7. The process according to claim 3, wherein the compound of formula II is crystallized from the alkanolic solvent as an alkanolic complex.

8. The process according to claim 5, wherein the compound of formula II is crystallized from the alkanolic solvent as an alkanolic complex.

9. A process for the preparation of a compound with formula III

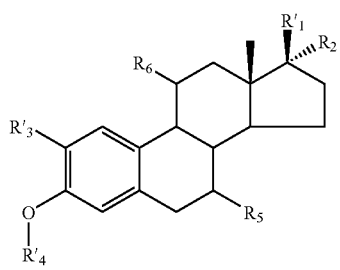

(III)

wherein $R'_1$ is an ester-group of the formula —O—C(O)—$R_7$, wherein $R_7$ represents hydrogen or an alkyl group having from 1 to 3 C atoms; $R_2$ is hydrogen or an hydrocarbyl group; $R'_3$ is a hydroxy group; $R'_4$ is a nitrobenzophenone group; and $R_5$ and $R_6$ independently are hydrogen or a hydroxy- or hydrocarbyl group; from a compound of formula II

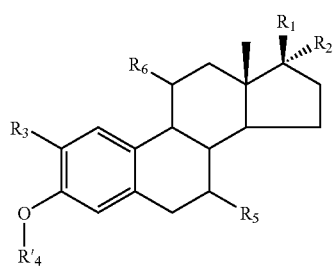

(II)

wherein $R_1$ is an hydroxy group; $R_2$ is hydrogen or an hydrocarbyl group; $R_3$ is hydrogen; $R'_4$ is a nitrobenzophenone group; and $R_5$ and $R_6$ independently are hydrogen or a hydroxy- or hydrocarbyl group;
wherein the compound of formula II is supplied as an alkanolic complex; and comprising the steps of acetylation and oxidation.

10. A one-pot process for the preparation of a compound with formula III

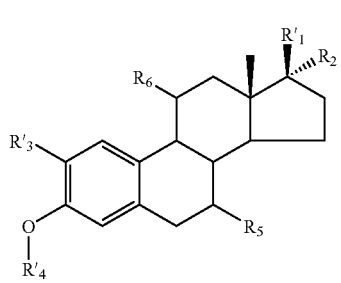

(III)

wherein $R'^1$ is an ester-group of the formula —O—C(O)—$R_7$, wherein $R_7$ represents hydrogen or an alkyl group having from 1 to 3 C atoms; $R_2$ is hydrogen or an hydrocarbyl group; $R'_3$ is a hydroxy group; $R'_4$ is a nitrobenzophenone group; and $R_5$ and $R_6$ independently are a hydrogen or a hydroxy- or hydrocarbyl group; from a compound of formula II

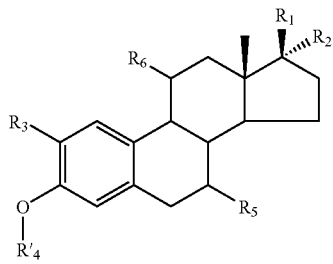

(II)

wherein $R_1$ is an hydroxy group; $R_2$ is hydrogen or an hydrocarbyl group; $R_3$ is hydrogen; $R'_4$ is a nitrobenzophenone group; and $R_5$ and $R_6$ independently are hydrogen or a hydroxy- or hydrocarbyl group; comprising a) esterification of the $R_1$ hydroxy group in the compound of formula II by reacting said compound with an excess of an acid anhydride of the formula $R_7$—C(O)—O—C(O)—$R_7$, wherein $R_7$ represents hydrogen or an alkyl group having from 1 to 3 C atoms, in the presence of a first acid, selected from phosphoric acid, sulphuric acid, hydrogen halides, sulphonic acids, and halogenated carboxylic acids, which first acid is soluble in the acid anhydride; yielding a reaction mixture containing the first acid, the 17β-ester-derivative of the compound of formula II, an acid of the formula HO—C(O)—$R_7$, wherein $R_7$ represents hydrogen or an alkyl group having from 1 to 3 C atoms, and residual acid anhydride;

b) addition of a sufficient amount of water to convert the residual acid anhydride to an acid of the formula HO—C(O)—$R_7$, wherein $R_7$ represents hydrogen or an alkyl group having from 1 to 3 C atoms; yielding a reaction mixture containing the first acid, the 17β-ester-derivative of the compound of formula II, the acid of formula HO—C(O)—$R_7$, and optionally any residual water;

c) addition of a second acid, yielding a reaction mixture containing a complex of said second acid and the 17β-ester-derivative of the compound of formula II; and d) oxidation of the $R_3$ hydrogen group in the 17β-ester-derivative by addition of an, optionally prepared in-situ, organic peroxoic acid, within a time period of 30 minutes; yielding a mixture comprising the compound of formula III, an acid of the formula HO—C(O)—$R_7$, wherein $R_7$ represents hydrogen or an alkyl group having from 1 to 3 C atoms, and optionally any residual water and/or organic peroxoic acid.

11. A process for the preparation of an 2-alkoxy-$\Delta^{1,3,5(10)}$-estratriene-derivative with formula V

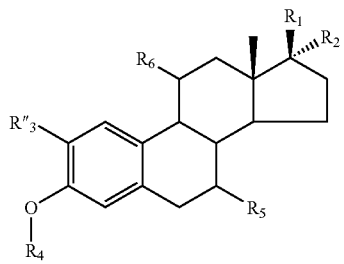

(V)

wherein $R_1$ is an hydroxy group; $R_2$ is hydrogen or an hydrocarbyl group; $R''_3$ is an alkoxy group; $R_4$ is hydrogen; and $R_5$ and $R_6$ independently are hydrogen or a hydroxy- or hydrocarbyl group; from a compound of formula I

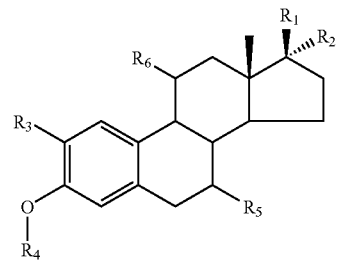

(I)

wherein, $R_1$, $R_2$, $R_4$, $R_5$ and $R_6$ are as defined above and $R_3$ is hydrogen, wherein a compound of formula II

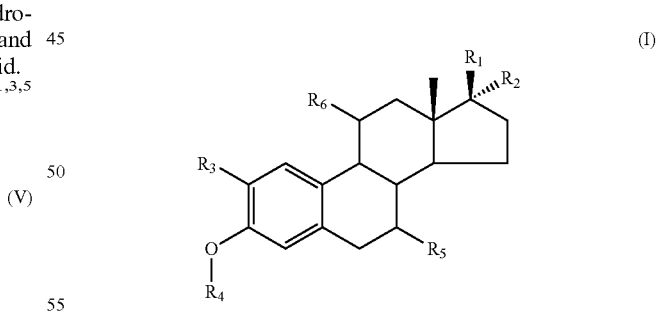

wherein $R_1$, $R_2$, $R_3$, $R_5$ and $R_6$ are as defined above and $R'_4$ is a nitrobenzophenone group;

is prepared from a compound of formula I (I)

wherein, $R_1$, $R_2$, $R_3$ $R_5$ and $R_6$ are as defined above and $R_4$ is hydrogen;

wherein the compound of formula I is reacted under alkaline conditions with 2-chloro-5-nitrobenzophenone in the presence of an alkanolic solvent and the compound of formula II is directly crystallized from this alkanolic solvent;

and wherein the compound with formula III

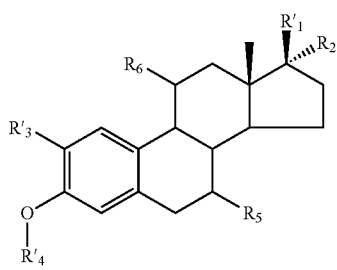

wherein R'$_1$ is an ester-group of the formula —O—C(O)—R$_7$, wherein R$_7$ represents hydrogen or an alkyl group having from 1 to 3 C atoms; R$_2$, R'$_4$, R$_5$ and R$_6$ are as defined above and R'$_3$ is an hydroxy group;
is prepared from a compound of formula II

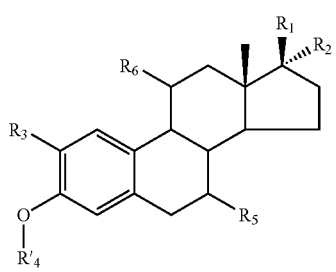

wherein R$_1$, R$_2$, R$_3$, R'$_4$, R$_5$ and R$_6$ are as defined above;
wherein the compound of formula II is supplied as an alkanolic complex; and comprising the steps of acetylation and oxidation;
and wherein
the compound of the formula III is alkylated and hydrolysed.

12. A process according to claim 11 for the preparation of a 2-alkoxy-derivate of 3,17β-estradiol (formula V) comprising the steps of
a) reacting 3,17β-estradiol (formula I) to 17β-hydroxy-Δ$^{1,3,5\ (10)}$-estratriene 3-(2-benzoyl-4-nitro)-phenyl ether (formula II);

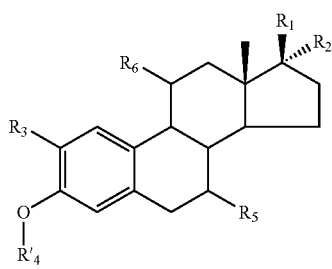

and
b) reacting the 17β-hydroxy-Δ$^{1,3,5\ (10)}$-estratriene 3-(2-benzoyl-4-nitro)-phenyl ether (formula II) to a 2-alkoxy-derivate of 3,17β-estradiol (formula V).

13. A complex of an alkanol and a compound of formula II

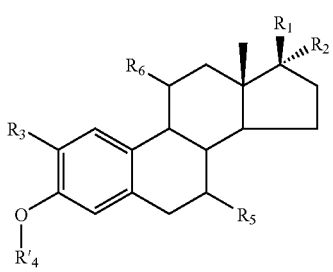

wherein R$_1$ and R$_2$ independently are hydrogen or a hydroxy- or hydrocarbyl group; or wherein R$_1$ and R$_2$ together are a double bonded oxygen; R$_3$ is hydrogen; R'$_4$ is a nitrobenzophenone group; and R$_5$ and R$_6$ independently are hydrogen or a hydroxy- or hydrocarbyl group;

obtainable from a process comprising crystallization of the compound of formula II from a solution of said alkanol.

14. The complex according to claim 13, wherein in the compound of formula II, R$_1$ is an hydroxy group and R$_2$ is hydrogen; or wherein R$_1$ and R$_2$ together are a double bonded oxygen; and wherein R$_5$ and R$_6$ are hydrogen groups.

15. The complex according to claim 13, wherein the alkanol is a C2-C6 mono-alkanol.

16. A complex of 17β-hydroxy-Δ$^{1,3,5\ (10)}$-estratriene 3-(2-Benzoyl-4-nitro)-phenyl ether and a C2-C6 mono-alkanol.

17. The complex according to claim 14, wherein the alkanol is a C2-6 mono-alkanol.

* * * * *